United States Patent [19]

Sauer

[11] Patent Number: 4,633,870

[45] Date of Patent: Jan. 6, 1987

[54] APPARATUS FOR EFFECTING ANASTOMOSIS OF TUBULAR TISSUE BY LASER WELDING

[76] Inventor: Jude S. Sauer, 6½ Lattimore Rd., Rochester, N.Y. 14620

[21] Appl. No.: 748,972

[22] Filed: Jun. 26, 1985

[51] Int. Cl.$^4$ ............ A61B 17/36; A61B 17/04; B23K 9/00
[52] U.S. Cl. .................. 128/303.1; 128/334 R; 219/121 LC; 219/121 LU
[58] Field of Search ............ 128/303.1, 335, 334 R, 128/305.1, 303 R; 219/121 LC, 121 LD, 121 LU, 121 LV; 408/701

[56] References Cited

U.S. PATENT DOCUMENTS

| | | | |
|---|---|---|---|
| 4,001,543 | 1/1977 | Bove et al. | 219/121 LC |
| 4,080,525 | 3/1978 | Gobetz | 219/121 LC |
| 4,143,660 | 3/1979 | Malyahev | 128/303.1 |

OTHER PUBLICATIONS

The Lancet, Oct. 6, 1986, K. K. Jain, Sutureless Extra-Intracranial Anastomois by Laser.
Barry Gross, "Laser Device Aids Vessel Surgery", Washington Post, Aug. 6, 1984, p. 21.

*Primary Examiner*—Richard C. Pinkham
*Assistant Examiner*—Gary Jackson
*Attorney, Agent, or Firm*—Shlesinger, Fitzsimmons & Shlesinger

[57] ABSTRACT

Two semi-cylindrical jaws, are releasably attachable around the abutting ends of a pair of tubular tissues that are held together by a tubular stent. A shuttle, which revolves in the jaws 360° around the outside of the junction of the tissues, is connected to a tubular conduit, that extends slidably through a handle on one of the jaws to the exterior of the instrument. The conduit contains at least three fiberoptic cords, the inner ends of which are connected to the shuttle for movement therewith, and to register with a mirror which, is also mounted on the shuttle. The outer ends of the cords are connected, respectively, to a light source for illuminating the seam which is to be welded, to a source of laser energy for directing a laser beam onto the seam, and to a lens which is utilized for observing the site where the welding is to take place. A cable, which extends slidably through the conduit, is connected in one embodiment to the mirror to reciprocate it relative to the shuttle for adjustment of the laser beam accurately onto the seam, in a second embodiment to the mirror to pivot it about an axis transverse to the tissue axes, and in a third embodiment to the inner ends of the cords to shift them relative to the mirror.

In use a light beam and a laser beam are directed through two cords onto the mirror in the shuttle, which reflects the beams onto the abutting ends of the tissues that are to be welded. After the cable has been manipulated to adjust the laser beam correctly onto the proposed seam, the entire conduit is shifted relative to the handle and jaw sections to revolve the shuttle a full 360° around the tissues thereby to laser weld their ends together along a circular seam.

17 Claims, 10 Drawing Figures

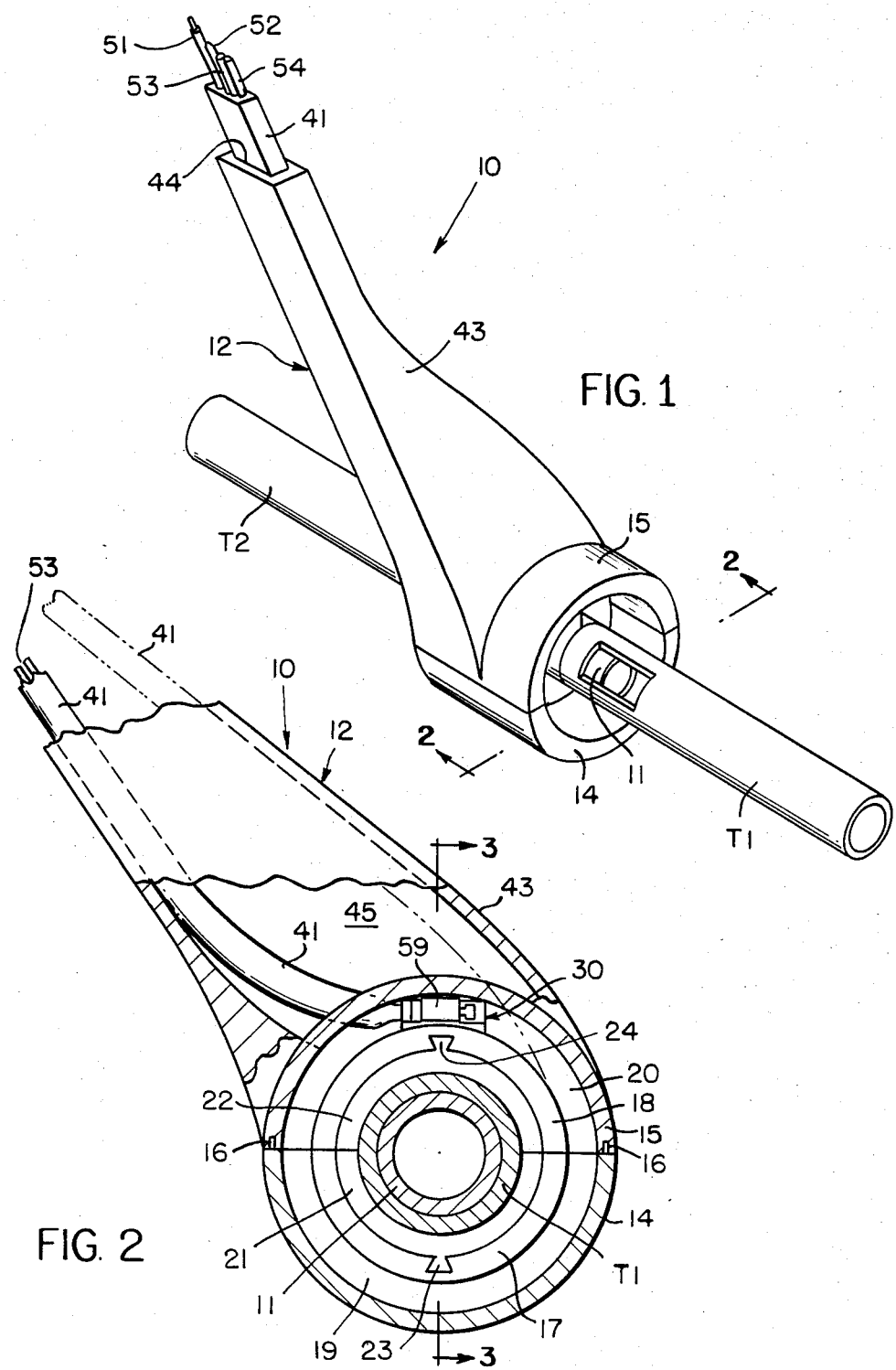

APPARATUS FOR EFFECTING ANASTOMOSIS OF TUBULAR TISSUE BY LASER WELDING

BACKGROUND OF THE INVENTION

This invention relates to a novel apparatus for effecting surgical anastomosis by means of laser welding. More specifically, this invention relates to novel surgical apparatus for directing a laser beam circumferentially around the juxtaposed ends of a pair of tubular tissues surgically to weld them together.

In recent years the use of laser technology in medicine and surgery has extended beyond its early use in the field of ophthamology, and is now being employed in general and tumor surgery, otolaryngology, orthopedic surgery, urology, etc. Most recently it has been used in connection with the welding of body tissues, as taught, for example, by U.S. Pat. No. 4,143,660, wherein a laser beam of the argon, carbon dioxide or neodymium garnet variety was directed by a flexible cord of light fibers linearly across the clamped section of a hollow organ, so as surgically to weld together the opposed side walls of the organ. The disadvantage of equipment of this type is that, because of its massive size, it can be used only to seam together, or perhaps to cut through the two superimposed tissue sections which are clamped together. With this type of apparatus, therefore, it is not possible to effect a satisfactory end-to-end anastomosis of tubular tissues, whereby the confronting ends of the tissues retain their tubular configurations.

Efforts heretofore have been made to use a carbon dioxide laser for sutureless anastomosis of fallopian tubes (von Klitzing L., Grosspietzsch R., Klink F., et al., "Surgical Refertilization by means of a Laser Technique", Fortschr-Med, 96 (7): 357–9, Feb. 16, 1978; and Klink F., Grosspietzsch R., von Klitzing L. et al., "Animal in Vivo studies and in Vitro experiments with human tubes for end-to-end anastomotic operation by a $CO^2$ laser technique", Fertil-Steril, 30 (1): 100–102, July, 1978); and a laser, rather than sutures has been used to achieve anastomosis in the case of extra-intracranial bypass operations (Jain KK: "Sutureless extra-intracranial anastomosis by laser", Letter to the Editor, the Lancet, 2(8406): 816–817, Oct. 6, 1984). Moreover, in certain cases a stent has been used to hold together the confronting ends of tubular tissues during sutureless anastomosis by laser welding, but the procedure has not been satisfactory, because it has been necessary manually to manipulate the tissues in order to expose the desired surfaces thereof to the laser beam. This makes it almost impossible to produce an accurate seam, and in many instances the procedure is precluded because of the very location of the tissues.

It is an object of this invention, therefore, to provide a novel apparatus for effecting a perfect end-to-end anastomosis of two tubular tissues by laser welding them together without causing any undesirable collapse of the confronting ends of the tissues, and without requiring any manual manipulation of the tissues during the welding operation.

A more specific object of this invention is to provide novel apparatus for manipulating a laser beam in a predetermined manner relative to human tissue in order to effect laser welding of the tissue in a predetermined manner, and along a predetermined circular path.

Other objects of this invention will be apparent hereinafter from the specification and from the recital of the appended claims, particularly when read in conjunction with the accompanying drawings.

SUMMARY OF THE INVENTION

To effect the end-to-end anastomosis of two tubular tissues, opposite ends of a tubular stent, which may be of the water soluble variety, and which has an outside diameter equal to the tubal intraluminal diameter of the tissues, are inserted into the confronting ends of the tissues. The confronting ends of the tissues are then shifted into engagement with each other, after which a laser beam is directed circumferentially around the abutting ends of the tissues for a full 360°, thereby surgically seaming or welding them together. The stent can be left to dissolve in due course, or depending upon the nature of the surgery, can be removed through an opening formed in one of the other of the tubular tissues at a point axially spaced from the welded ends.

For use in directing the laser beam onto the abutting ends of the tubular tissues, three fiberoptic cords are employed, one to direct light (illumination) onto the ends of the tubular tissues which are to be welded, a second to convey reflected light from the situs of the operation to the eye of an observer (surgeon), and a third to direct a laser beam from a source onto the tissues. (One or more additional fiberoptic cables can be employed, if desired, for using one or more additional laser beams or sighting devices.) In addition, the equipment contains a hand manipuable guide mechanism, which is disposed to be clamped around the outside of the abutting ends of the tubular sections that are to be welded together, and which contains cable-operated means for moving one end of each of the fiberoptic cables circumferentially around the outside of the abutting ends of the tubular tissues to enable examination thereof, and to direct the laser beam onto the site to effect the welding together of the abutting ends.

THE DRAWINGS

FIG. 1 is a perspective view showing one embodiment of a laser welding instrument in an operative position relative to a pair of tubular tissues that are to be seamed together;

FIG. 2 is an enlarged, fragmentary sectional of the view of this instrument taken generally along the line 2—2 in FIG. 1 looking in the direction of the arrows;

DETAILED DESCRIPTION OF THE PREFERRED EMBODIMENTS

Figure 3:
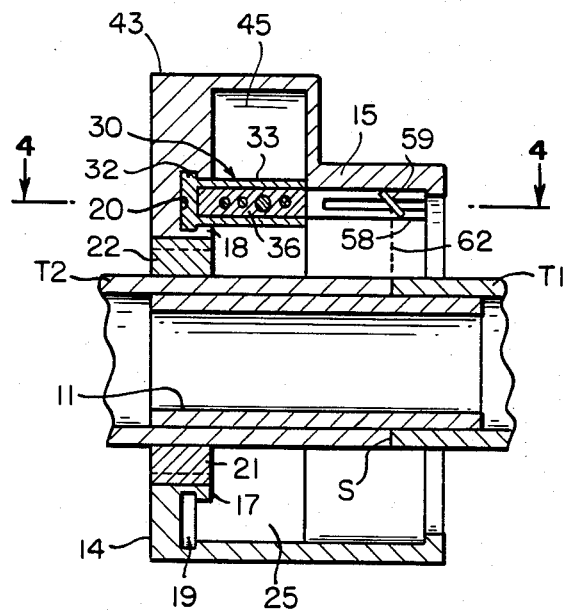
FIG. 3 is a fragmentary sectional view taken generally along the line 3—3 in FIG. 2 looking in the direction of the arrows.

Referring now to the drawings by numerals of a reference, and first to the embodiment shown in FIGS. 1-5, numeral 10 denotes generally a hand manipuable surgical instrument for the laser welding of tubular tissues. In this Fig. the confronting ends of two tubular tissues T1 and T2, which are to be joined together, are removably secured together by a tubular stent 11, opposite ends which have been inserted manually and coaxially into confronting ends of the tissues. (A portion of tissue T1 has been cut away in FIG. 1 better to illustrate the disposition of stent 11.) Instrument 10 comprises a two-piece housing 12 including a lower, generally semi-cylindrical jaw section 14, and an upper, similarly shaped and complimentary jaw section 15, which is releasably attached by pins 16 to section 14.

Adjacent one end thereof (the left end in FIG. 3) section 14 has in its bore an internal semi-cylindrical shoulder 17, which registers with and is complimentary to a similar shoulder 18 formed in section 15. Shoulders 17 and 18 extend axially inwardly from one end of sections 14 and 15 (the left ends in FIG. 3) for a portion only of the axial lengths of the respective sections and have formed in their inner ends arcuate slots or tracks 19 and 20, respectively, which are generally T-shaped in cross section. Releasably secured coaxially to and overlying the inner peripheral surfaces of shoulders 17 and 18 are two, complimentary, arcuate tissue clamps 21 and 22, respectively. Projecting from the outer peripheral surfaces of clamps 21 and 22 are tongues 23 and 24, respectively, which are slidably disposed in registering grooves or slots in the inner peripheral surfaces of shoulders 17 and 18 releasably to secure the clamps 21 and 22 thereto.

When the jaw sections 14 and 15 are secured together, as shown for example in FIG. 2, the complimentary tracks or slots 19 and 20 form a full, circular track which surrounds and is radially spaced from the portion of tissue T2 which passes through the center of clamps 21, 22. Mounted in this track to travel, as noted hereinafter, a full 360° around tissue T1 is a shuttle or carrier 30, the details of which are shown more clearly in FIGS. 4 and 5.

Carrier 30 comprises a plastic shuttle or housing 31 having a flanged end section 32 slidably guided for travel in the registering, T-shaped ends of tracks 19 and 20, and an integral, arcuate, cart-supporting section 33, which projects out of track 19, 20, and into an annular passage 25 (FIG. 3) formed in the interconnected jaw sections 14, 15 adjacent their shoulders 17, 18. As shown more clearly in FIG. 5, the opposed edges or sides of the shuttle sections 32 and 33 are appropriately curved to conform to the curvature of tracks 19 and 20.

Secured in a rectangularly shaped slot 34 (FIGS. 4 and 5), which is formed in the shuttle section 33 to open on the side thereof remote from section 32, is a rectangularly shaped cart 36. Cart 36 has a pair of right annular intersecting side edges 37 and 38 (FIG. 4), the former of which registers with the side of passage 25 remote from the track 19, 20, and the latter of which lies in a plane extending transversely of the track 19, 20.

Secured at one end to the cart surface 38 is an elongate, flexible conduit 41, which is adapted to be manipulated as noted hereinafter to move the carrier or shuttle 30 circumferentially around track 19, 20. Conduit 41 extends through an opening in jaw section 15 into the lower end of a hollow handle section 43 which projects generally radially from a portion of the outer peripheral surface of section 15 on one end thereof. Handle section 43 of instrument 10 has therethrough an elongate bore 44, which is generally rectangular in cross section, and the height or thickness of which increases gradually as the bore 44 approaches section 15, thereby forming in the handle section an enlarged chamber 45 which comminucates with passage 25.

Conduite 41 contains a plurality of cords or cables, four of which are denoted in the illustrated embodiment at 51, 52, 53 and 54, respectively. These cords extend out of the lower or inner end of conduit 41 and into registering, spaced, arcuate bores 51', 52', 53' and 54', respectively, which are formed in the cart 36 to open at one end on surface 37 and at their opposite ends on surface 38.

Figure 4:
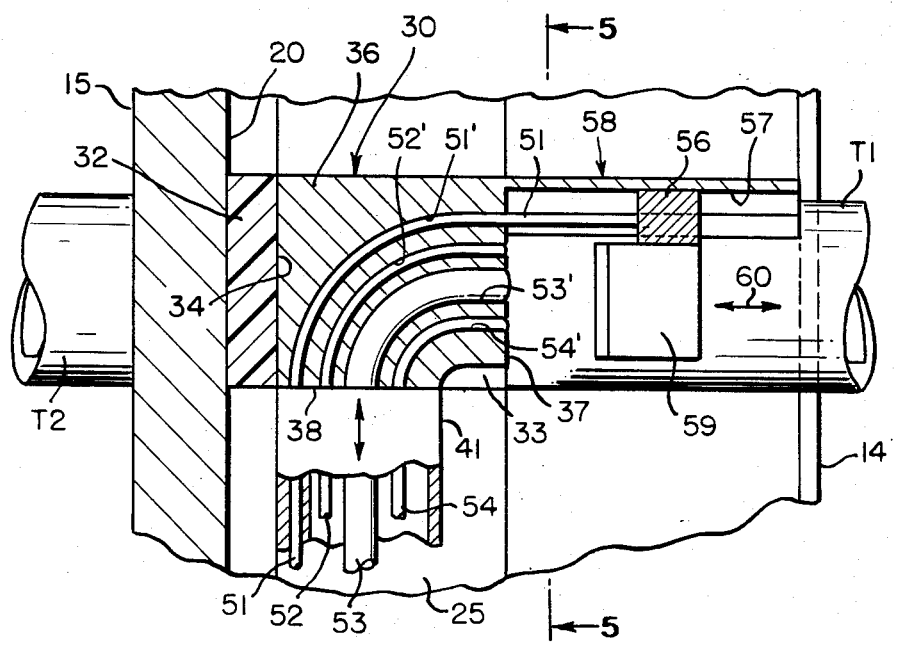
FIG. 4 is a greatly enlarged fragmentary sectional view taken gnerally along the line 4—4 in FIG. 3.
Figure 5:
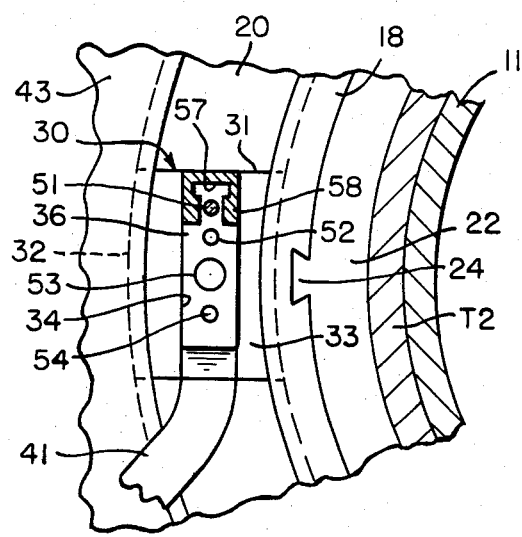
FIG. 5 is a fragmentary sectional view taken generally along the line 5—5 in FIG. 4, looking in the direction of the arrows.

Cord 51 is in the form of a flexible wire or cable that extends just beyond the cart surface 37 and is attached to a reciprocable mirror support bracket 56 (FIG. 4). Bracket 56 has a generally T-shaped end slidably guided in a correspondingly shaped groove 57, which is formed in an arm 58 that is integral with and extends from the cart 36 adjacent one end thereof (the upper end as shown in FIG. 4). Secured to the opposite end of bracket 56 with the reflecting surface thereof confronting upon and inclined to the cart surface 37 is a mirror 59. The cord 51, the upper end of which extends out of the conduit 41 (FIG. 1), consists of an elongate, flexible wire of cable, which is longitudinally slidable in the conduite 41 and the registering bore 51' in the cart 36, so that the bracket 56 and its attached mirror 59 can be shifted longitudinally of arm 58 toward and away from the cart surface 37, and in the direction indicated by the arrows 60 in FIG. 4.

Cords 52, 53, and 54, however, are secured against movement in their registering bores 52', 53', and 54' in the cart 36. Moreover, as shown more clearly in FIG. 4, the inner terminal ends of these cords open on the cart surface 37, so that they are directed toward the reflective surface of mirror 59. Each of the cords 52, 53 and 54 is made of a flexible, fiberoptic material for conveying light energy to or from the reflective surface of mirror 59. In practice, for example, cord 52 is adapted to have its upper end connected externally of handle section 43 to a light source for directing illumination through cord 52 onto the surface of mirror 59. As shown more clearly in FIG. 3, the surface of mirror 59 is inclined in such manner that light from cord 52 is reflected by the mirror radially inwardly of the jaw sections 14 and 15 in the direction indicated by the broken line 62 in FIG. 3, and onto the confronting ends of the tissues T1 and T2.

The cord 53 is substantially larger in diameter than the light emitting cord 52, and has in its terminal end a series of conventional focusing mirrors (not illustrated), which open on the cart surface 37 so as to register substantially centrally with the mirror 59. Cord 53 conveys reflected light and images from the mirror surface 59 rearwardly through the conduit 41 to the eye of an observer (not illustrated), and thus provides means for viewing the site where the laser welding is to take place.

The remaining fiberoptic cord 54 is adapted to be connected at its upper or outer end to a source of laser energy which, as noted hereinafter, is then adapted to be directed through the cord 54, onto the surface of mirror 59, and then to be reflected downwardly by the mirror onto the confronting ends of the tissues T1 and T2 to effect surgical welding of the tissues together along a seam denoted at S in FIG. 3. In order to effect this seam circumferentially around the juxtaposed ends of the tissues, the operator carefully manipulates the upper end of the conduit 41 by shifting it longitudinally relative to the handle section 43 of the instrument.

At the outset, for example, when the desired laser beam has been directed through the cord 54 onto the mirror 59, the surgeon urges conduit 41 inwardly into the handle section 43, thereby imparting a force tangentially to the cart 36, and hence to the attached shuttle housing 31. The carrier 30 is therefore caused to travel clockwise in track 19, 20 from its starting or full line position in FIG. 2 for a full 360° around shoulders 17, 18 until the carrier 30 reaches a substantially identical position as shown in FIG. 2, except that at this moment the conduit 41 will have been flipped or shifted from its full line position to its broken line position. (FIG. 2) in which it comes to rest against the surface of of the chamber 45 opposite to that engaged by the conduit when it is in its starting position. During this travel the laser beam will have been directed by the mirror 59 onto the juncture of the tissues along a plane containing the seam S as shown in FIG. 3, thereby laser welding together the confronting ends of the tissues along a full, circular path.

After the seam S has been completed, the conduit 41 is withdrawn from the handle section 43 to shift the carrier 30 back to its starting position as shown in FIG. 2; and, the lower jaw section 14 is separated from the upper jaw section 15 so that the instrument can be withdrawn from around the now-welded tisues. If the stent 11 is made from a water soluable matter it may be left within the tissues eventually to dissolve; or alternatively, the stent can be removed surgically through an opening made in one or the other of the tissues at a point axially spaced from the seam S, or through any pre-existing, nearby opening.

If when next used the instrument 10 is to be applied to tissues having diameters larger or smaller than those illustrated in the drawings, the clamps 21, 22 can be removed and replaced by clamps having different internal diameters, either larger or smaller, depending upon the sizes of the tissues to be welded. Also, if desired, simple spacers could be interposed between the confronting surfaces of the jaw sections 14, 15 and clamp sections 21, 22 in order to increase, if necessary, the maximum diameter between the clamps and jaws. Although this would tend to create more of an oval path or track 19, 20, nevertheless the carrier 30 would be guided in such track to travel 360° about the tissues to enable the laser welding together of the confronting ends thereof in a manner similar to that described above.

Also, it will be readily apparent that the cable operated bracket 56 provides a means for shifting the mirror 59 longtiudinally or axially relative to the tissues that are to be welded together, thereby to permit the light or laser beams to be directed properly onto the juxtaposed tissue ends which are to be welded together. Thus it is necessary only to placed the clamp sections 14, 15 around the tissues and the enclosed stent in such manner that the confronting ends of the tissues lie somewhere between the right ends of the jaw sections as shown in FIG. 3, and the inner ends of the associated shoulders 17, 18. Thereafter the mirror can be shifted by its cable 51 until, as viewed by the cord 53, the mirror properly overlies the area that is to be welded.

Figure 6:
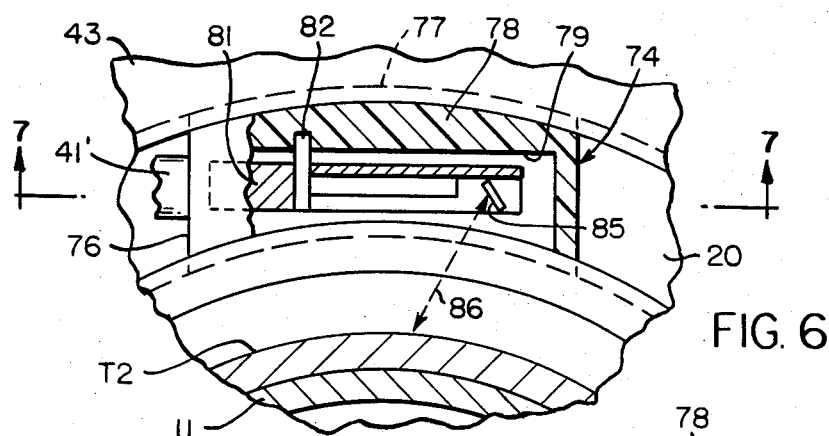
FIG. 6 is a fragmentary sectional view generally similar to FIG. 5 but showing a modified form of this instrument.
Figure 7:
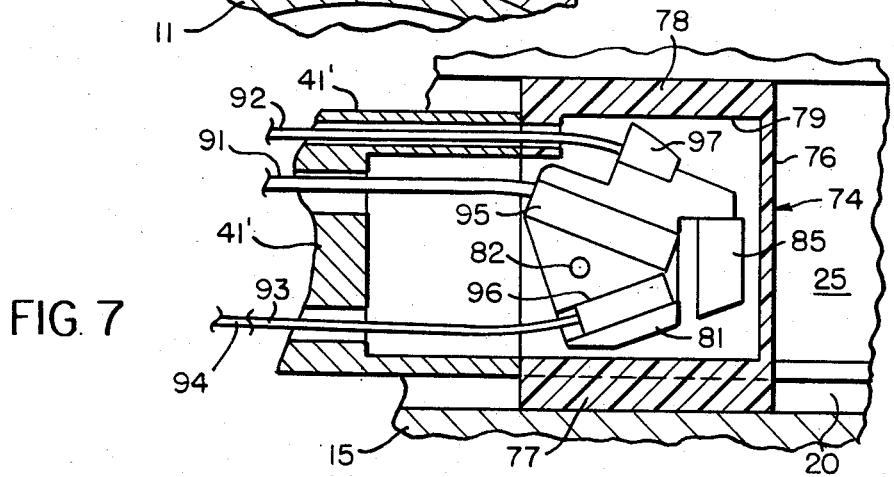
FIG. 7 is a fragmentary sectional view taken generally along the line 7—7 in FIG. 6, but on a slightly smaller scale.

Referring now to the embodiment shown in FIGS. 6 and 7, wherein like numbers are employed to denote elements similar to those employed in the first embodiment, 74 denotes generally a modified carrier which, as noted hereinafter, is designed to travel in the annular space 25 circumferentially around the outside of a pair of tissues T1 and T2, when the latter are connected by a stent 11 and clamped between the clamps 21 and 22 as described in the first embodiment.

Carrier 74 comprises a plastic shuttle 76 having a curved, generally T-shaped end 77, which is mounted for sliding movement in the registering tracks 19 and 20 of jaw sections 14 and 15, and a recessed body section 78, which projects transversely from the curved end 77 across the space 25. Section 78 has in its inner surface, or the under-side thereof as shown in FIG. 6, a large recess 79 containing a mirror supporting plate 81. Adjacent one end thereof (the left end in FIGS. 6 and 7) plate 81 is pivotally connected by a pin 82 to the body section 78 of the shuttle for limited pivotal movement in recess 79 about an axis that extends normal to the axis about which the shuttle 76 revolves in the track 19,20.

Mounted on the underside of the plate 81 adjacent its end remote from pin 82 is a mirror 85, the reflective surface of which faces radially inwardly of the instrument, and which is inclined to the pivotal axis of plate or support 81 in order to direct light, as noted hereinafter, radially inwardly along the line 86 (FIG. 6) toward the axial center-line of the tissues T1, T2 that are to be laser welded together.

Secured at its inner end to the side of shuttle 76 remote from mirror 85 is the carrier operating conduit 41', which is generally similar to that of conduit 41 in the first embodiment. Conduit 41' carries four cords or cables 91, 92, 93 and 94. Cable 91 is a fiberoptic viewing cord which projects slidably into shuttle 76 where it is fixed in a boss 95 on plate 81 so that its terminal end is disposed in spaced, confronting relation to the mirror 85. Fiberoptic cords 93 and 94 likewise extend one above the other slidably into shuttle 76 where they are fixed in another boss 96 on plate 81 so that their inner, terminal ends also are disposed in spaced, confronting relation to mirror 85. The remaining cord 92 is a wire cable which also extends slidably through the adjacent wall of shuttle 76 and is attached as at 97 to the plate 81 adjacent one side thereof.

In use, the ends of the fiberoptic cords 93 and 94 remote from support 81 are disposed to be connected to a light source and to a laser source, respectively, whereby light is directed by cord 93 onto mirror 85 and by the latter onto the tissues T1 and T2 to illuminate the site where the laser welding is to take place. A laser beam, in turn, is directed by cord 94 against mirror 85 to be reflected by the latter also toward the tissues. The cord 91 is used in a manner similar to cord 53 in the first embodiment to observe the welding site; and cable 92, which is slidably mounted in conduit 41', can be manipulated to pivot plate 81 back and forth about pin 82 until the laser beam reflected from mirror 85 is directed precisely onto the desired location of the welded seam.

When the laser beam from cord 94 has been properly positioned by manipulation of cable 92, the conduit 41' is then shifted relative to handle section 43 in a manner similar to conduit 41, thereby to cause carrier 74 to be revolved a full 360° around the tissues T1, T2, during which time the laser beam welds the desired seam to secure together the confronting ends of the tissues. Thereafter jaws 14 and 15 are separated and the instrument is withdrawn from the patient's body. The stent is then left to dissolve, or is surgically removed as in the case of the first embodiment.

Figure 8:
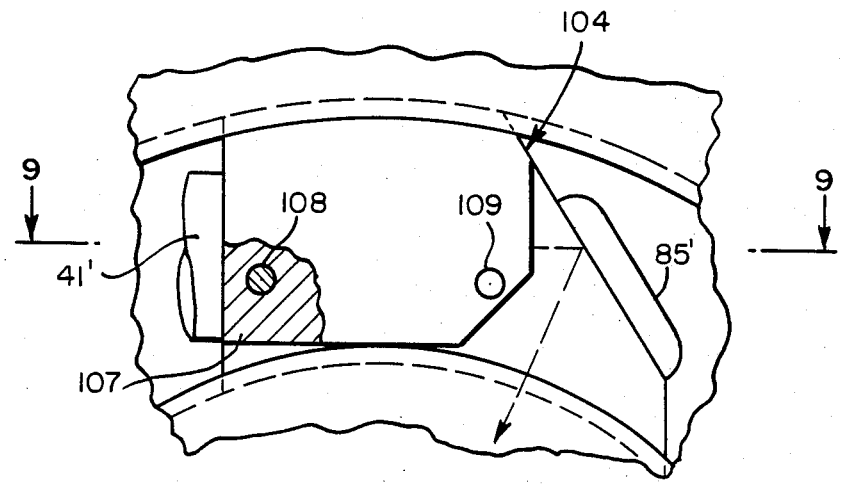
FIG. 8 is a fragmentary section generally similar to FIG. 6 but showing still another modification of this invention.
Figure 9:
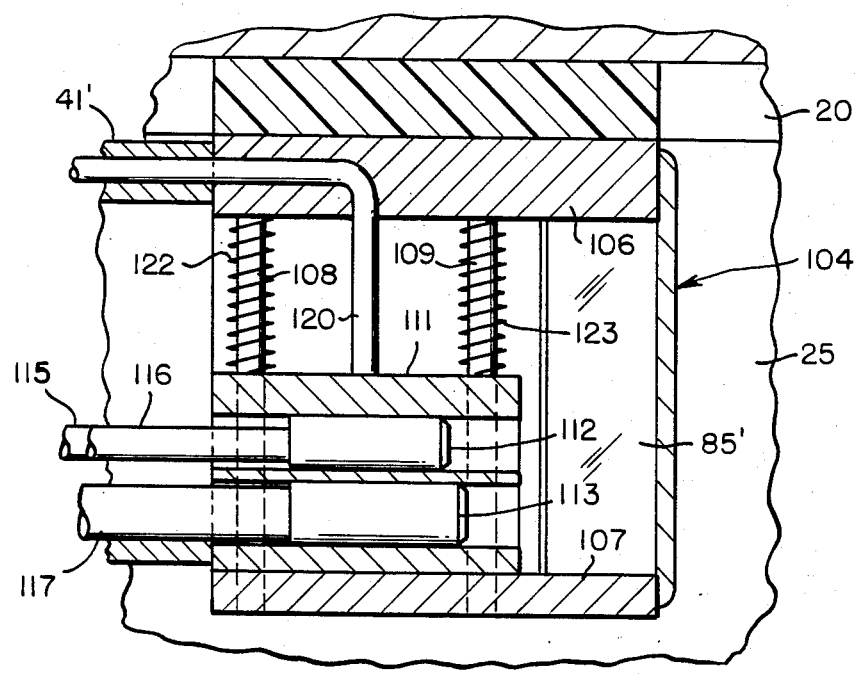
FIG. 9 is a fragmentary sectional view taken generally along the line 9—9 in FIG. 8.

In the embodiment shown in FIGS. 8 and 9, the numeral 104 denotes another type of carrier having a mirror 85' which is fixed to and extends between a pair of spaced, paralled sidewalls 106 and 107 of the shuttle body. Slidably mounted on a pair of spaced, parallel pins or rods 108 and 109, which extend between the shuttle walls 106, 107, is a movable cable support 111. Support 111 has fixed thereon a pair of spaced, tubular bosses 112 and 113, which at one end face mirror 85', and at their opposite ends the operating conduit 41'. Two fiberoptic cables, which project from conduit 41', are secured in boss 112 to have their terminal ends face mirror 85' for use in directing thereon light (illuminating) and laser beams, respectively. A fiberoptic viewing cord 117 is secured in the other boss 113; and an operating cable 120, which is fixed to one side of 111, extends therefrom slidably through an opening in wall 106 into conduit 41' for slidable adjustment relative to conduit 41' and carrier 104.

In use, the carrier 104 can be shifted by conduit 41' in passage 25 in the same manner as the previous embodiments. To adjust the postion of reflected beams relative to the welding site, cable 120 is shifted relative to conduit 41', thereby shifting support 111 and the attached cables laterally relative to mirror 85'. To assist in advancing support 111 from wall 106 to wall 107, coiled compression springs 123 are mounted around pins 108 and 109 between wall 106 and support 111.

Figure 10:
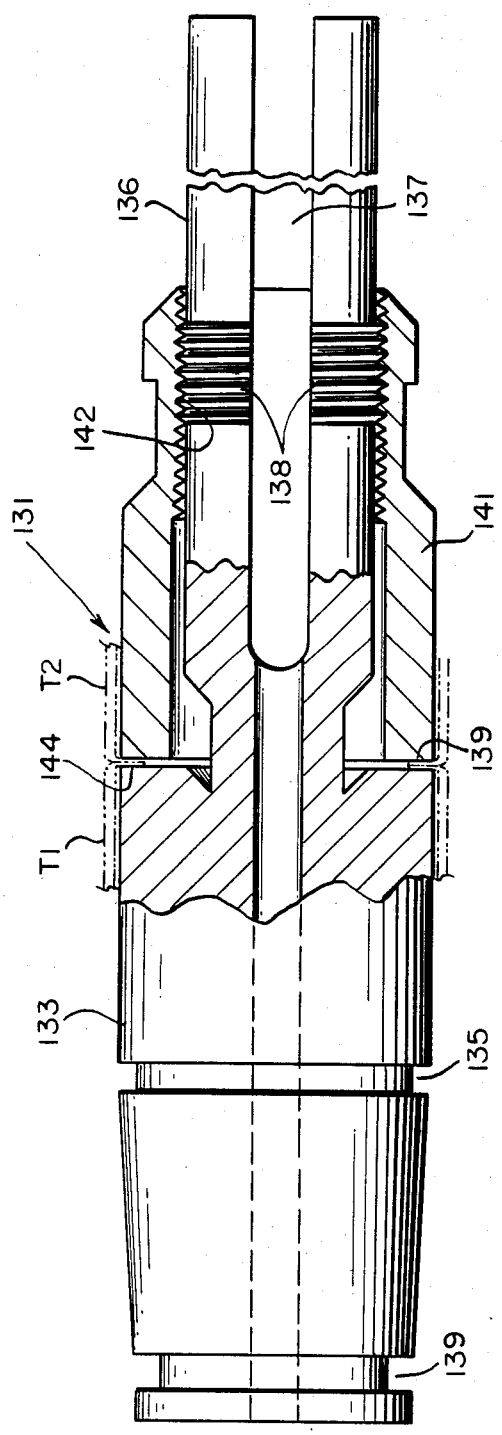
FIG. 10 is an enlarged, longitudinal sectional view of a modified form of stent which may be used with this invention, portions of the stent being shown in full.

FIG. 10 illustrates a modified, two-piece stent 131 comprising a first, cylindrically-shaped section 133 having a pair of spaced, annular grooves 134 and 135 formed in its peripheral surface adjacent one end thereof, and having a reduced-diameter bifurcated projection 136 on its opposite end which is slotted as at 137. Releasably secured on the bifurcated end 136 of section 133 is a sleeve section 141 having adjacent one end thereof an internally-threaded bore section 142, which is threaded onto externally threaded sections 138 of projection 137. At its opposite end sleeve section 141 has a transverse face 139 which confronts upon and registers with a transverse shoulder 144, which is formed on section 133 at the juncture of its main section with its reduced-diameter projection 136.

In use tissues T1 and T2, which are shown fragmentarily and in phantom by broken lines in FIG. 10, are drawn over opposite ends of the stent 131 and have their confronting ends folded into a space between the confronting surfaces 139 and 144 on the stent sections 133 and 141. The latter two sections may, of course, be adjusted relative to each other by rotating the sleeve section 141 on the extension 136. The two grooves 134 and 135 on section 133 may be gripped by registering ribs on the clamps 21 and 22 to secure the stent against movement relative to instrument 10.

From the foregoing it will be apparent that the present invention provides relatively simple and inexpensive and accurate methods and apparatus for effecting laser anastomosis of tubular tissues without having to manipulate tissues during the laser welding procedure. Moreover, instruments of the type disclosed herein can be made small enough to permit insertion into the smallest of cavities in the human body to effect anastomosis of most tubular tissues, including veins, arteries, fallopian tubes, intestines, bile ducts, etc. While in the preferred embodiments disclosed herein it has been suggested that instruments be employed in connection with the end-to-end anastomosis of tubular tissues, it will be readily apparent that the instruments could be used for end-to-side procedures, or for repairing other tissues, such for example, tendons, peripheral nerves, etc. Moreover, while the above-noted instruments have included a fiberoptic cable for conveying only a single laser beam to the site of the procedure, it will be readily apparent that, if desired, still another fiberoptic cord could be incorporated in each instrument to convey selectively to the site a second laser beam, such as a $CO_2$ laser beam for use in cutting through tissues, thereby to separate the tissues rather than to weld them together. Also, of course, movements of the instruments or its movable parts could be machine enhanced, if desired.

There are a number of surgical devices which are capable of generating the laser beam which is applied to the cords 54 and 94 of the illustrated embodiment. The Neodimium, Yag, Argon-dye and copper/gold lasers can provide the laser energy for distribution by fiberoptic cords. The $CO_2$ laser apparatus, which has been used in laser microsurgery is capable of producing $CO_2$ laser energy densities ranging from 50 to 250 $J/cm^2$, the densities which have proved in the past to be suitable for the laser welding together of rabbit tissues. Low-powered $CO_2$ lasers of this variety have also been used successfully in welding together severed tissues of experimental animals such as rats. ("Laser-assisted Vas Anastomosis" A preliminary report") Charles M. Lynn, M.D., et al., Lasers in Surgery and Medicine 3:261–263, 1983). However, because of the large wave length of $CO_2$ laser energy, satisfactory optic fibers therefor are not yet commercially available. The exact means for generating the laser beam for use in connection with applicant's herein disclosed instruments, it will be understood, is a matter of choice and forms no part of the instant invention.

In addition to the previously noted prior art, there are U.S. Pat. Nos. 3,769,117 and 4,143,261 which suggest devices for effecting relative rotation between a laser beam and oval-shaped workpieces, and some devices for laser welding stationary pipe (U.S. Pat. Nos. 4,080,525 and 4,001,543), but these references were not at all concerned with surgical procedures. U.S. Pat. No. 4,367,017 discloses a laser beam reflecting system for welding purposes, or the like, but requires at least three, spaced reflecting surfaces. U.S. Pat. No. 4,326,118 discloses apparatus for laser welding end flanges to semicylindrical shells, but produces, therefore, only a semicircular seam.

While this invention has been illustrated and described in connection with only certain embodiments, it will be apparent that it is capable of still further modification, and that this application is intended to cover any such modifications as may fall within the scope of one skilled in the art, or the appended claims.

I claim:

1. A surgical instrument for the external laser welding of tissues, comprising
    a hand manipulable housing having first and second sections movable relative to each other selectively to form a central opening through said housing,
    means for releasably supporting a pair of generally cylindrically shaped tissue sections in said central opening upon formation thereof, and with confronting ends of said tissues abutting each other along a seam located within said central opening, a first, flexible, light transmissive element extending at one end into said housing and disposed to be connected at its opposite end to a source of laser energy operable to direct a beam of laser energy through said first element into said housing, and means in said housing for directing said laser beam from said one end of said first element to said central opening and onto said seam, said beam directing means including means for moving said beam around the abutting ends of said tissue sections thereby to weld together said abutting ends along said seam, and said housing sections being movable away from each other at the conclusion of a welding operation, thereby to permit withdrawal of the housing laterally from the welded tissues to disengage the latter.

2. A surgical instrument as defined in claim 1, wherein said means for moving said beam includes means mounting said one end of said first element for circular travel in said housing at least approximately 360° around said central opening and the abutting ends of the tissue sections positioned therein.

3. A surgical instrument as defined in claim 2, wherein said means mounting said one end of said first element comprises a carrier mounted in said housing to revolve coaxially of said central opening around the outside of said tissue sections, and having thereon a reflective surface facing inwardly of said central opening toward said seam, said one end of said first element being connected to said carrier to revolve therewith and to have the terminal end thereof disposed in spaced, confronting relation with said reflective surface, and said reflective surface lying in a plane inclined to the axis of the laser beam emanating from said one end of said first element, and being operative to reflect said beam onto said seam.

4. A surgical instrument as defined in claim 3, wherein one of said housing sections comprise an elongate, hollow handle section having therethrough a longitudinally extending bore opening at one end on said central opening in said housing and at its opposite end on the exterior of said housing, an elongate, flexible actuator extends slidably through the bore in said handle section and has an inner end fixed to said carrier and an outer end extending out of said handle section, and said actuator is reciprocable relative to said handle section to revolve said carier selectively in opposite directions in said central opening.

5. A surgical instrument as defined in claim 4, including first and second means mounting said reflective surface, and said terminal end of said first element, respectively, on said carrier for limited adjustment thereon one relative to the other properly to align said reflected beam with said seam, and cable means operatively connected at one end to one of said first and second mounting means and projecting at its opposite end slidably through said handle section to the exterior of said housing, said cable means being shiftable relative to said handle section to adjust one of said first and second mounting means as may be necessary to direct the reflected laser beam onto said seam.

6. A surgical instrument as defined in claim 5, wherein said first mounting means supports said reflective surface on said carrier for limited reciprocable movement parallel to the axis of said central opening.

7. A surgical instrument as defined in claim 4, wherein said housing sections comprise, a first jaw section integral with said handle section and having therein an internal peripheral surface defining one portion of said central opening, and a second jaw section having therein an internal peripheral surface complimentary to said internal peripheral surface on said first jaw section, and means is provided for releasably securing said jaw sections together with said internal peripheral surfaces thereof disposed in registering, coaxial relation, and operatively defining said central opening in said housing.

8. A surgical instrument as defined in claim 5, wherein said first mounting means supports said reflective surface on said carrier for pivotal movement about an axis extending transversely of the axis of said central opening.

9. A surgical instrument as defined in claim 5, wherein said second mounting means supports said terminal end of said first element on said carrier for limited reciprocable movement parallel to the axis of said central opening.

10. A surgical instrument as defined in claim 1, wherein said first element comprises a fiberoptic cord, said beam directing means comprises a carrier attached to one end of said cord and mounted in said housing to revolve around said central opening, and a mirror is mounted on said carrier in spaced, confronting relation to said one end of said cord and is operative to reflect a laser beam therefrom onto said seam.

11. A surgical instrument as defined in claim 10, including at least two additional fiberoptic cords each of which has one end therof secured to said carrier in spaced, confronting registry to said mirror and has the opposite end thereof projecting externally of said housing, one of said additional cords being disposed to have said opposite end thereof connected to a light source to direct a beam of light onto said mirror for use in illuminating the seam which is to be welded, and another of said cords being larger in diameter than the remaining cords, and being disposed to direct an image of the seam through said opposite end thereof, and into the eye of an observer.

12. A surgical instrument as defined in claim 11, including means mounting said mirror on said carrier for limited adjustment relative thereto in order properly to align reflected light from said mirror onto said seam, and vice versa, and a further cord in the form of a flexible wire connected at one end to said mirror and projecting slidably at its opposite end out of said housing for adjustment relative thereto.

13. A surgical instrument as defined in claim 12, wherein said housing sections include an elongate, hollow handle section for manipulating the instrument relative to said tissue sections, an elongate, flexible conduit is attached at one end to said carrier and projects slidably at its opposite end through said handle section to the exterior of said housing, and said conduit is reciprocable relative to said housing selectively to shift said carrier in opposite directions about the axis of said central opening and the tissue sections therein.

14. A surgical instrument as defined in claim 13, wherein said cords extend from said carrier longitudinally through the bore in said conduit to the exterior thereof.

15. A surgical instrument for use in the laser welding of tissues, comprising.

a housing having a recess in one end thereof, means on said housing for releasably securing a tissue to said housing in registry with said recess, a carrier mounted on said housing for movement in opposite directions adjacent said recess, means on said carrier for directing a laser beam onto said tissue during movement of said carrier in one direction thereby surgically to weld the tisssue along a predetermined seam, said beam directing means comprising a first, flexible light transmissive cord having one end thereof connected to said carrier for movement therewith, and having the opposite end thereof projecting to the exterior of said carrier for connection to a source of laser energy operable to direct a beam of laser energy through said cord and out of said one end thereof, and two additional, flexible, light transmissive cords each of which has one end connected to said carrier in optical communication with said tissue, and each of which projects at its opposite end exteriorly of said carrier, one of said additional cords being disposed to be connected at said opposite end thereof to a light source for illuminating the tissue secured to said housing, and the other of said additional cords being disposed to project an image of said tissue to the eye of an observer.

16. A surgical instrument as defined in claim 15, including a flexible conduit connected at one end to said carrier and mounted intermediate its ends on said housing for reciprocation relative thereto, and thereby selectively to move said carrier in opposite directions, said beam directing means including a mirror mounted on said carrier adjacent said one end of said first cord, and operative to reflect a laser beam therefrom onto said tissue, and means mounting said one ends of all of said cords on said carrier for movement therewith and in unison with each other.

17. A surgical instrument as defined in claim 16, including means for adjusting one of said mirror and said mounting means, respectively, relative to the other mounting means, thereby properly to align the reflected laser beam with the desired portion of said tissue.

* * * * *